US011445949B2

(12) United States Patent
Fujisaki et al.

(10) Patent No.: US 11,445,949 B2
(45) Date of Patent: Sep. 20, 2022

(54) SENSOR AND VITAL SIGN INFORMATION PROCESSING SYSTEM

(71) Applicant: NIHON KOHDEN CORPORATION, Tokyo (JP)

(72) Inventors: Hideki Fujisaki, Tokorozawa (JP); Kazumasa Ito, Tokorozawa (JP); Naoki Kobayashi, Tokorozawa (JP); Kumi Sugiyama, Tokorozawa (JP); Tetsuo Suzuki, Tokorozawa (JP); Masahiro Takeuchi, Tokorozawa (JP); Jiongxun Chen, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 426 days.

(21) Appl. No.: 16/014,710

(22) Filed: Jun. 21, 2018

(65) Prior Publication Data

US 2018/0368746 A1    Dec. 27, 2018

(30) Foreign Application Priority Data

Jun. 23, 2017    (JP) .............................. JP2017-123298

(51) Int. Cl.
*A61B 5/1455*    (2006.01)
*G16H 40/40*    (2018.01)
(Continued)

(52) U.S. Cl.
CPC ........ *A61B 5/14552* (2013.01); *A61B 5/1113* (2013.01); *A61B 5/25* (2021.01); *G16H 40/40* (2018.01); *A61B 5/0006* (2013.01); *A61B 5/0024* (2013.01); *A61B 5/02438* (2013.01); *A61B 5/6801* (2013.01)

(58) Field of Classification Search
CPC . A61B 5/14552; A61B 5/1113; A61B 5/0408; A61B 5/0006; A61B 5/6801; A61B 5/0024; A61B 5/02438; G16H 40/40; G06Q 50/24; G06F 19/30
See application file for complete search history.

(56) References Cited

U.S. PATENT DOCUMENTS 5,368,224 A    11/1994    Richardson et al.
5,555,882 A    9/1996    Richardson et al.
(Continued)

FOREIGN PATENT DOCUMENTS

JP    3958353 B2    8/2007
WO    94-09698 A1    5/1994

*Primary Examiner* — Devin B Henson
*Assistant Examiner* — Justin Xu
(74) *Attorney, Agent, or Firm* — Pearne & Gordon LLP

(57) ABSTRACT

A vital sign information processing system includes a sensor configured to be attached to a living body, and an information acquisition apparatus configured to acquire vital sign information of the living body through the sensor. A first memory is disposed in the sensor and stores first site information indicative of a site at which the sensor is to be used. A second memory is disposed in the information acquisition apparatus and stores second site information indicative of a site at which the information acquisition apparatus is to be used. A processor disposed in the information acquisition apparatus causes the information acquisition apparatus to perform notification when the first site information and the second site information are not matched.

13 Claims, 3 Drawing Sheets

(51) Int. Cl.
   *A61B 5/11*    (2006.01)
   *A61B 5/25*    (2021.01)
   A61B 5/00     (2006.01)
   A61B 5/024    (2006.01)

(56) References Cited

U.S. PATENT DOCUMENTS

| | | |
|---|---|---|
| 5,713,355 A | 2/1998 | Richardson et al. |
| 5,885,213 A | 3/1999 | Richardson et al. |
| 8,112,136 B2* | 2/2012 | Mannheimer .......... A61B 5/053 600/323 |
| 9,949,676 B2* | 4/2018 | Al-Ali ................ A61B 5/14551 |
| 10,070,805 B1* | 9/2018 | Friedman ................ A61B 5/002 |
| 2002/0124295 A1* | 9/2002 | Fenwick ............ A61B 5/02055 2/69 |
| 2003/0195644 A1* | 10/2003 | Borders ............... A61G 13/107 700/90 |
| 2015/0080011 A1* | 3/2015 | Zelinka ................ H04W 4/029 455/456.1 |
| 2016/0151022 A1* | 6/2016 | Berlin ................. A61B 5/7246 600/301 |
| 2018/0353111 A1* | 12/2018 | Buxton ................ A61B 5/0004 |
| 2021/0110920 A1* | 4/2021 | Heyes .................... G16H 20/10 |

* cited by examiner

SENSOR AND VITAL SIGN INFORMATION PROCESSING SYSTEM

CROSS-REFERENCE TO RELATED APPLICATION

The present application claims priority from Japanese Patent Application No. 2017-123298 filed on Jun. 23, 2017, the entire content of which is incorporated herein by reference.

BACKGROUND

The presently disclosed subject matter relates to a sensor configured to be attached to a living body to acquire vital sign information, and to communicate with an information acquisition apparatus. The presently disclosed subject matter relates also to a vital sign information processing system having the information acquisition apparatus and the sensor.

Examples of a related art vital sign information processing system include a bedside monitor system (see, e.g., JP3958353B2). A bedside monitor system has an SpO2 probe, an example of a sensor, and a bedside monitor, an example of an information acquisition apparatus. The SpO2 probe is configured to be attached to a living body, and to be communicably connected to the bedside monitor. The bedside monitor is configured to acquire vital sign information through the SpO2 probe, and to calculate the arterial oxygen saturation (SpO2) of the living body.

Medical facilities can include many sites. A site means a place having a specific purpose of use. Examples of a site include a critical care medicine area, an intensive care unit, a neonatal intensive care unit, an operating room, a laboratory, a hospital ward, and an MRI room.

An information acquisition apparatus like the one described above is installed in each site. A sensor like the one described above can be connected to an information acquisition apparatus installed in any site in so far as they are compatible under a same standard. Therefore, a situation may occur where a sensor used for a certain patient at a certain site is moved together with the patient to another site, and then connected to another information acquisition apparatus at the other site. As a result, an unintended variation may occur in stock information of sensors at each site.

There is also a possibility that the sensor moved to the other site is erroneously used. For example, a sensor for a neonate may be attached to a child.

SUMMARY

The presently disclosed subject matter prevents a sensor for acquiring vital sign information from being erroneously used.

According to an aspect of the presently disclosed subject matter, a vital sign information processing system includes a sensor configured to be attached to a living body, an information acquisition apparatus configured to acquire vital sign information of the living body through the sensor, a first memory disposed in the sensor, the first memory storing first site information indicative of a site at which the sensor is to be used, a second memory disposed in the information acquisition apparatus, the second memory storing second site information indicative of a site at which the information acquisition apparatus is to be used, and a processor disposed in the information acquisition apparatus. The processor causes the information acquisition apparatus to perform notification when the first site information and the second site information are not matched.

According to another aspect of the presently disclosed subject matter, a sensor is configured to be attached to a living body to acquire vital sign information, and is communicable with an information acquisition apparatus. The sensor includes a memory configured to store information indicative of a site at which the sensor is to be used.

DETAILED DESCRIPTION

Hereinafter, an embodiment of the presently disclosed subject matter will be described in detail with reference to the drawings.

Figure 1:
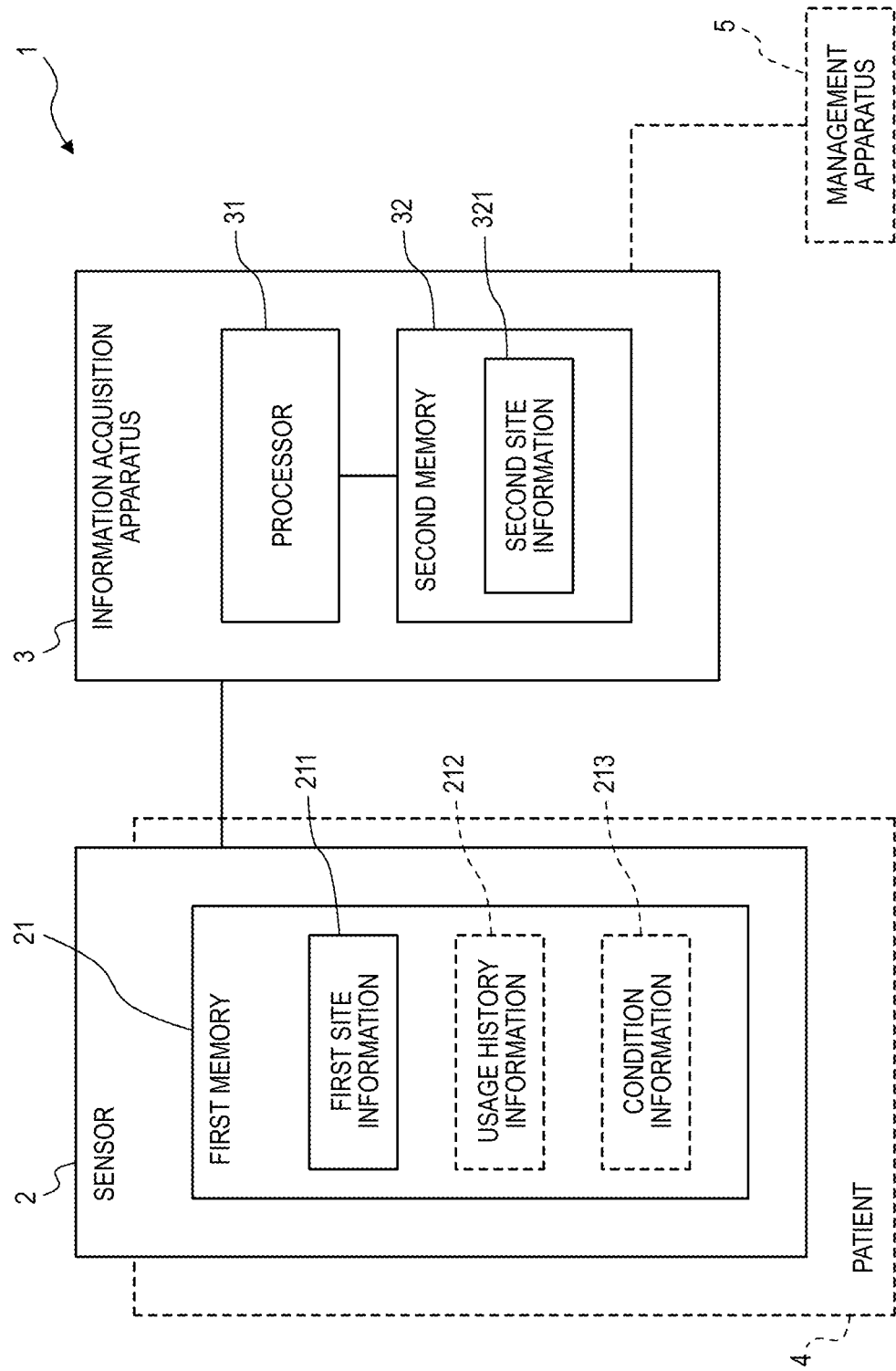
FIG. 1 is a block diagram illustrating a functional configuration of a vital sign information processing system according to an embodiment of the presently disclosed subject matter.

FIG. 1 is a diagram illustrating a functional configuration of a vital sign information processing system 1 according to an embodiment of the presently disclosed subject matter. The vital sign information processing system 1 includes a sensor 2 and an information acquisition apparatus 3. The sensor 2 is configured to be attached to a patient 4 (an example of the living body). The information acquisition apparatus 3 is configured to acquire vital sign information of the patient 4 through the sensor 2. That is, the sensor 2 is configured to communicate with the information acquisition apparatus 3.

Examples of the sensor 2 include an SpO2 probe for acquiring the arterial oxygen saturation of the patient 4 as vital sign information, electrocardiogram electrodes for acquiring an electrocardiogram of the patient 4 as vital sign information, brain wave electrodes for acquiring the brain wave of the patient 4 as vital sign information, a cuff for acquiring the non-invasive blood pressure of the patient 4 as vital sign information, and the like. Examples of the information acquisition apparatus 3 include a bedside monitor and the like.

The sensor 2 includes a first memory 21. The first memory 21 may include a semiconductor memory and the like. The first memory 21 stores first site information 211 indicative of one or more sites where the sensor 2 is to be used. Examples of the one or more sites include a critical care medicine area, an intensive care unit, a neonatal intensive care unit, an operating room, a laboratory, a hospital ward, and an MRI room.

The first site information 211 may be written by a user via an information writing apparatus before using the sensor 2. The information acquisition apparatus 3 may be configured to function as the information writing apparatus. In a case where the sensor 2 is designed for specific use (e.g., a sensor which can be used only in an operating room), the first site information may be previously written during manufacturing.

The information acquisition apparatus 3 includes a processor 31 and a second memory 32. Examples of the processor 31 include a CPU and an MPU. The second memory 32 may include a semiconductor memory, a hard disk drive, or the like. The second memory 32 stores second site information 321 indicative of one or more sites where the information acquisition apparatus 3 is to be used.

The second site information 321 may be written by a user via an information writing apparatus before installing the information acquisition apparatus 3. In a case where the information acquisition apparatus is designed for specific use (e.g., an apparatus which can be used only in an operating room), the second site information may be previously written during manufacturing.

Figure 2:
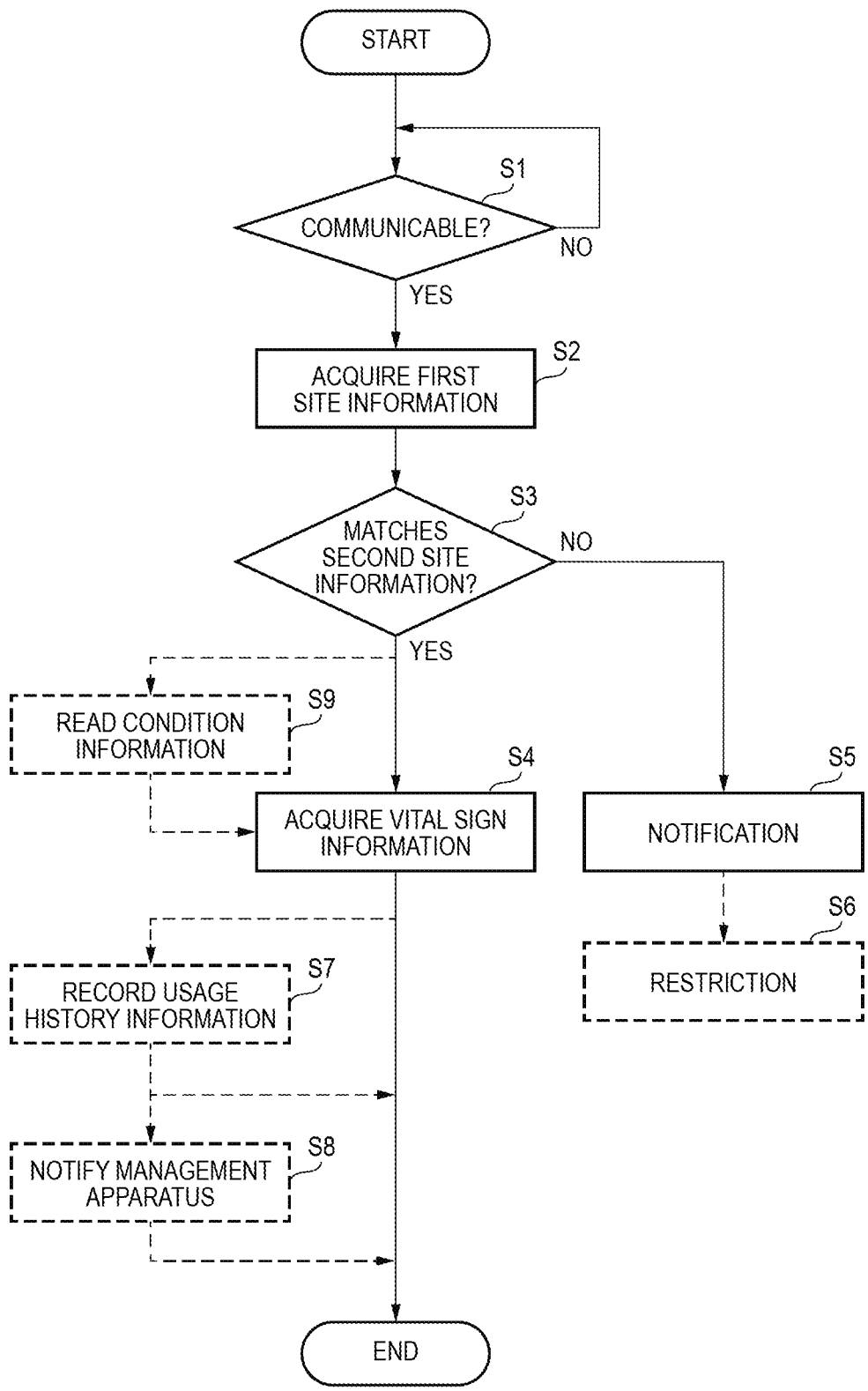
FIG. 2 is a flowchart illustrating an example of a process to be performed by an information acquisition apparatus of the vital sign information processing system.

FIG. 2 illustrates a process to be performed by the information acquisition apparatus 3 under control of the processor 31. The process is performed when the processor 31 executes instructions stored in a memory (a ROM, a RAM, or the like).

First, the processor 31 causes the information acquisition apparatus 3 to determine whether a condition that enables communication with the sensor 2 is met (step S1). If the communicable condition is not met (N in step S1), the information acquisition apparatus 3 is caused to repeat the determination until this condition is met.

If the condition that enables the communication with the sensor 2 is met (Y in step S1), the processor 31 causes the information acquisition apparatus 3 to acquire the first site information 211 (step S2). The information acquisition apparatus 3 acquires the first site information 211 from the first memory 21 of the sensor 2.

Next, the processor 31 causes the information acquisition apparatus 3 to compare the first site information 211 and the second site information 321 with each other (step S3). The information acquisition apparatus 3 compares the first site information 211 acquired from the sensor 2, with the second site information 321 stored in the second memory 32.

If, as a result of the comparison, it is determined that the first site information 211 and the second site information 321 are matched (Y in step S3), the processor 31 causes the information acquisition apparatus 3 to acquire vital sign information of the patient 4 (step S4). The information acquisition apparatus 3 acquires vital sign information of the patient 4 through the sensor 2.

If, as a result of the comparison, it is determined that the first site information 211 and the second site information 321 are not matched (N in step S3), the processor 31 causes the information acquisition apparatus 3 to perform a notification process (step S5). For example the site indicated by the first site information 211 is a neonatal care unit, and that indicated by the second site information 321 is a hospital ward, for example, the information acquisition apparatus 3 performs notification.

The comparison result that the first site information 211 and the second site information 321 are matched indicates a fact that the sensor 2 is used at a proper site. In contrast, the comparison result that the first site information 211 and the second site information 321 are not matched indicates a fact that the sensor 2 not originally existed at the site is, for some reason, in communication with the information acquisition apparatus 3. For example, it is possible that the sensor 2 that was used with another patient at another site has been moved together with this patient to the site at which the information acquisition apparatus 3 is installed.

The notification process may cause a user to recognize this fact, and urge the user to replace the sensor 2. The notification may be at least one of visual notification, audible notification, and haptic notification. Examples of the notification process include a generation of an alarm sound, a lighting of an indicator, a display of a message, a generation of vibration, and the like. This can prevent the sensor 2 from being erroneously used.

The notification performed by the information acquisition apparatus 3 may include the first site information 211. For example, if the first site information 211 indicates a neonatal care unit, and the second site information 321 indicates a hospital ward, the information acquisition apparatus 3 may produce the notification that includes information indicating that the sensor 2 being used should originally be used in a neonatal care unit.

According to this configuration, it is possible to prompt a user to return the sensor 2 that should not be used at a site where the information acquisition apparatus 3 is installed, to the original site. This can prevent the sensor 2 from being erroneously used, and also correct an unintended variation in the stock of sensors at each site.

When the notification process is performed, as indicated by the broken line in FIG. 2, the processor 31 may control the information acquisition apparatus 3 to perform a restriction process (step S6). In the restriction process, the use of the sensor 2 communicating with the information acquisition apparatus 3 is restricted. Examples of the restriction process include an immediate prohibition of the use of the sensor 2, a setting of limitation of the number of usable times of the sensor 2, a continuous output of a notification message, and the like.

According to this configuration, it is possible to suppress a situation where a user continues to use the sensor 2 that should not exist at the site where the currently-communicating information acquisition apparatus 3 is installed. Therefore, the effect of prevention of erroneous use of the sensor 2 is enhanced.

The first site information 211 stored in the first memory 21 of the sensor 2 may include a plurality of sites where the sensor 2 can be used.

According to this configuration, the sensor 2 is allowed to be shared among the plurality of sites. For example, at sites among which a patient is moved relatively frequently, such as an operating room and an intensive care unit, an operation in which the same sensor is allowed to be used at both sites is more efficient. This enables a flexible operation while preventing the sensor 2 from being erroneously used.

As indicated by the broken line in FIG. 2, the processor 31 may control the information acquisition apparatus 3 to record information of usage history (step S7). As indicated by the broken lines in FIG. 1, the information acquisition apparatus 3 may record the second site information 321 indicative of the site at which it is installed, in the first memory 21 of the sensor 2 as usage history information 212. The usage history information 212 is readable by the information acquisition apparatus 3 or an information processing device.

The usage history information 212 is particularly effective in a case where the sensor is used while being moved among a plurality of sites (i.e., in a case where the first site information 211 includes a plurality of sites). By allowing a user to check, at the end of operation, the usage history information, the user can easily return the sensor to the site to which the sensor should belong. Therefore, it is possible to suppress an unintended variation in the stock of sensors at each site.

The recording of the usage history information 212 by the information acquisition apparatus 3 can be performed at any timing after the communication with the sensor 2 is enabled.

It is however preferable that, as shown in FIG. 2, the recording be performed after vital sign information is acquired.

By doing so, it is possible to prevent a situation where, when a user erroneously attaches a sensor to the information acquisition apparatus 3 instead of a sensor that should originally be used, unintended usage history information 212 is recorded. If it is recorded after the acquisition of vital sign information, there is a high likelihood that the sensor used for the acquisition is intentionally connected to the information acquisition apparatus 3. In order to achieve a same or similar effect, the usage history information 212 may be recorded when a period of time of communication between the sensor 2 and the information acquisition apparatus 3 reaches a threshold.

If, as a result of the comparison process (step S3) performed by the information acquisition apparatus 3, the first site information 211 and the second site information 321 are not matched, and the usage history information 212 is recorded in the first memory 21 of the sensor 2, the notification by the information acquisition apparatus 3 may include the usage history information 212. The usage history information 212 may be displayed by the information acquisition apparatus 3, or output in the form of a printed report or the like.

The notification of the usage history information 212 is particularly effective in a case where the sensor is used while being moved among a plurality of sites (i.e., in a case where the first site information 211 includes a plurality of sites). By checking the notified usage history information 212, the user can not only become aware of the site to which the sensor is to be returned, and but also use this information in investigating a cause of an erroneous movement.

In a case where a sequence of sites indicated by the usage history information 212 as the sites at which the sensor 2 have been used matches a predetermined sequence, the processor 31 may cause the information acquisition apparatus 3 to perform the notification. The predetermined sequence may be a sequence which never happens in a usual medical procedure flow, or a sequence which must not exist. An example of such a sequence is a sequence in which an intensive care unit is followed by a critical care medicine area.

This configuration is particularly effective in a case where the sensor is used while being moved among a plurality of sites (i.e., in a case where the first site information 211 includes a plurality of sites). A movement of the sensor among the sites at which the sensor is allowed to be used but in a sequence that should not occur can be notified.

For example, in a case where the sensor 2 in which a critical care medicine area and an intensive care unit are stored as the first site information 211 is moved from the intensive care unit to the critical care medicine area, notification will not be performed only by a comparison with the second site information 321. When the usage history information 212 indicates the movement from the intensive care unit to the critical care medicine area, however, this impermissible movement of the sensor 2 can be identified.

As indicated by the broken line in FIG. 1, the information acquisition apparatus 3 can be communicably connected to an external management apparatus 5. With this configuration, as indicated by the broken line in FIG. 2, the processor 31 can control the information acquisition apparatus 3 to perform the notification process (step S8). The information acquisition apparatus 3 notifies the management apparatus 5 of the usage history information 212 that has been read from the first memory 21 of the sensor 2.

According to this configuration, a set of usage history information notified from the information acquisition apparatuses 3 installed in respective sites can be centrally managed by the management apparatus 5. This makes it easy to manage the stock of sensors a each site, and to monitor the actual use of the sensors.

As indicated by the broken line in FIG. 1, condition information 213 may be stored in the first memory 21 of the sensor 2. The condition information 213 includes information indicative of operating conditions of the information acquisition apparatus 3. Examples of the condition information 213 include background information of the patient 4 (e.g., age, disease, risk factors, applied treatments, and the like), and information of characteristics of the sensor 2 (a product number, use conditions, the number of uses, and the like).

If, as a result of the comparison process (step S3) performed by the information acquisition apparatus 3, the first site information 211 and the second site information 321 are matched, the processor 31 controls the information acquisition apparatus 3 to read the condition information 213 in the first memory 21 (step S9). The processor 31 controls the information acquisition apparatus 3 to acquire vital sign information based on setting according to the condition information 213. In the information acquisition apparatus 3, for example, measurement conditions according to the background information of the patient 4 and the characteristic information of the sensor 2 may be set automatically.

According to this configuration, even in a case where the sensor 2 is moved among a plurality of sites, and connected to different information acquisition apparatuses 3, identical information acquisition conditions can be easily set. This reduces a burden on a medical person relating to the setting, and improves the accuracy of acquisition of vital sign information.

Figure 3:
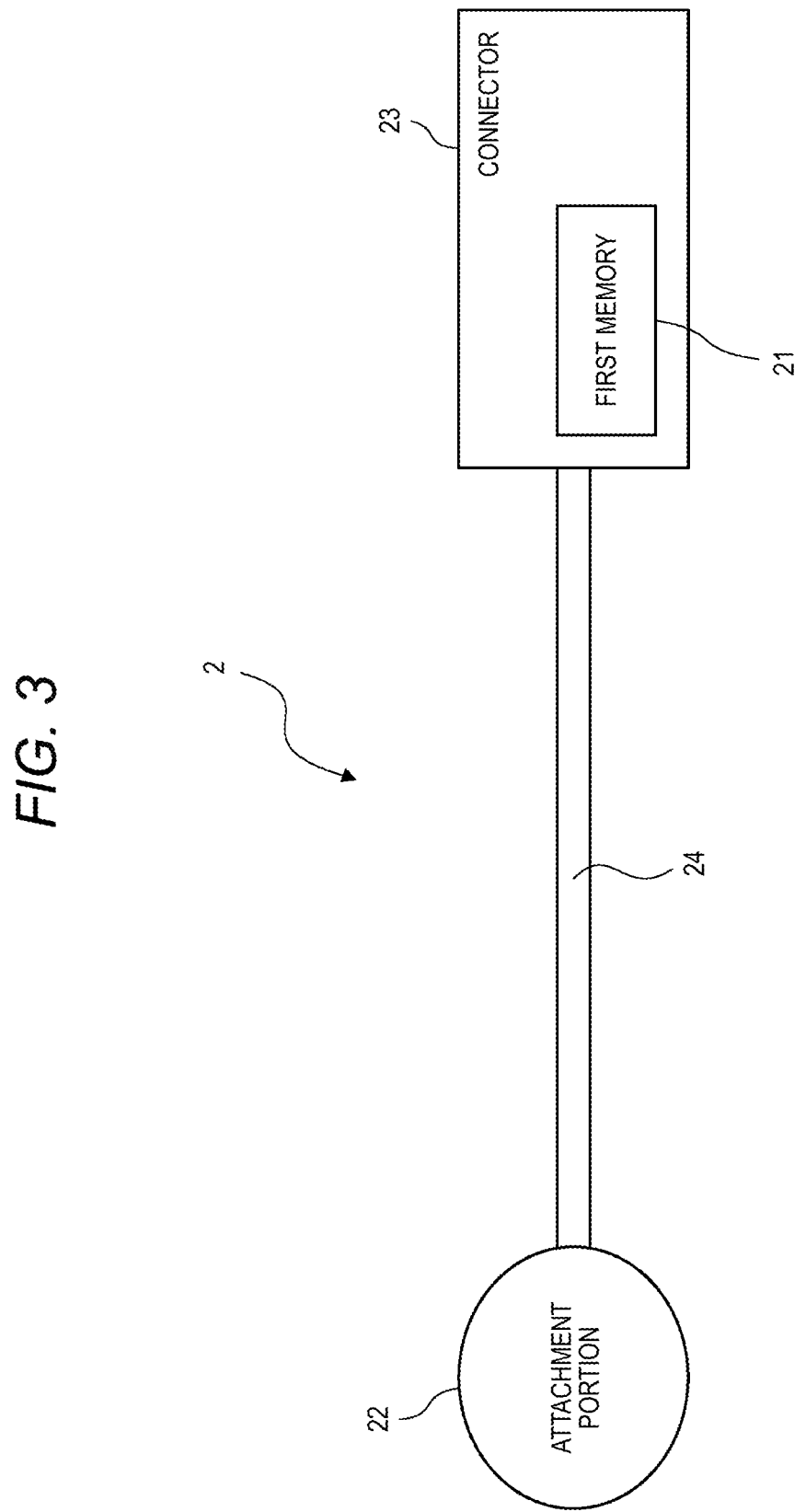
FIG. 3 is a diagram illustrating an example of a configuration of a sensor of the vital sign information processing system.

FIG. 3 illustrates an example of the configuration of the sensor 2. The sensor 2 may include an attachment portion 22, a connector 23, and a cable 24. The attachment portion 22 is configured to be attached to the body of the patient 4, and includes a sensor device. The connector 23 is configured to allow the sensor to communicate with the information acquisition apparatus 3. The connector 23 may be directly connected to the information acquisition apparatus 3, or indirectly connected through a junction cable or the like. The cable 24 connects the attachment portion 22 to the connector 23. The cable 24 incudes a power supply line and signal lines necessary for acquisition of vital sign information.

In this example, the first memory 21 is preferably disposed in the connector 23 which is necessary for enabling communication with the information acquisition apparatus 3, so that the size of the attachment portion 22 to be attached to the body of the patient 4 can be prevented from being increased. That is, while providing the first memory 21 storing information for preventing the sensor 2 from being erroneously used, it is possible to prevent the patient 4 from feeling bothersomeness.

While the presently disclosed subject matter has been described with reference to a certain embodiment thereof, it will be understood by a person skilled in the art that various changes and modifications can be made therein.

FIG. 1
2 SENSOR
3 INFORMATION ACQUISITION APPARATUS
4 PATIENT
5 MANAGEMENT APPARATUS
21 FIRST MEMORY
31 PROCESSOR

32 SECOND MEMORY
211 FIRST SITE INFORMATION
212 USAGE HISTORY INFORMATION
213 CONDITION INFORMATION
321 SECOND SITE INFORMATION
FIG. 2
START
S1 COMMUNICABLE?
S2 ACQUIRE FIRST SITE INFORMATION
S3 MATCHES SECOND SITE INFORMATION?
S4 ACQUIRE VITAL SIGN INFORMATION
S5 NOTIFICATION
S6 RESTRICTION
S7 RECORD USAGE HISTORY INFORMATION
S8 NOTIFY MANAGEMENT APPARATUS
S9 READ CONDITION INFORMATION
END
FIG. 3
21 FIRST MEMORY
22 ATTACHMENT PORTION
23 CONNECTOR

What is claimed is:

1. A vital sign information processing system comprising:
a sensor configured to be attached to a living body;
an information acquisition apparatus configured to acquire vital sign information of the living body through the sensor;
a first memory disposed in the sensor, the first memory storing first site information indicative of a site at which the sensor is to be used;
a second memory disposed in the information acquisition apparatus, the second memory storing second site information indicative of a site at which the information acquisition apparatus is to be used; and
a processor disposed in the information acquisition apparatus,
wherein the processor causes the information acquisition apparatus to perform a notification when the first site information and the second site information are not matched,
wherein the notification is a visual notification, an audible notification, or a haptic notification,
wherein the processor is configured to prohibit use of the sensor or limit a number of uses of the sensor, when the first site information and the second site information are not matched, and
wherein the first site information is stored in the first memory during manufacturing of the sensor,
wherein the site at which the sensor is to be used is a critical care medicine area, an intensive care unit, a neonatal intensive care unit, an operating room, a laboratory, a hospital ward, or a magnetic resonance imaging (MRI) room.

2. The vital sign information processing system according to claim 1, wherein the notification includes the first site information.

3. The vital sign information processing system according to claim 1, wherein, when the notification is performed, the processor causes the information acquisition apparatus to restrict a use of the sensor.

4. The vital sign information processing system according to claim 1, wherein the first site information is indicative of a plurality of sites at which the sensor is to be used.

5. The vital sign information processing system according to claim 1, wherein the processor records the second site information, as usage history information, in the first memory.

6. The vital sign information processing system according to claim 5, wherein the processor records the second site information in the first memory after the vital sign information is acquired through the sensor.

7. The vital sign information processing system according to claim 5, wherein the notification includes the usage history information.

8. The vital sign information processing system according to claim 5, wherein the processor causes the information acquisition apparatus to perform notification in a case where a sequence of sites at which the sensor has been used and indicated by the usage history information matches a predetermined sequence.

9. The vital sign information processing system according to claim 5, wherein the processor causes the information acquisition apparatus to notify an external management apparatus of the usage history information.

10. The vital sign information processing system according to claim 1, wherein condition information indicative of operating conditions of the information acquisition apparatus is stored in the first memory, and,
wherein in a case where the first site information and the second site information are matched, the processor causes the information acquisition apparatus to acquire the vital sign information, based on a setting according to the operating conditions.

11. The vital sign information processing system according to claim 1, wherein the sensor comprises an attachment portion configured to be attached to the living body, and a connector configured to allow communication with the information acquisition apparatus, wherein the first memory is disposed in the connector.

12. The vital sign information processing system according to claim 1, wherein the vital sign information includes an arterial oxygen saturation.

13. The vital sign information processing system according to claim 1, wherein the first memory further stores condition information including background information of the living body.

* * * * *